(12) United States Patent
Phillips et al.

(10) Patent No.: US 10,314,994 B2
(45) Date of Patent: Jun. 11, 2019

(54) BRIDLE CATHETER

(71) Applicant: Applied Medical Technology, Inc., Brecksville, OH (US)

(72) Inventors: Grant Wesley Phillips, Richfield, OH (US); Derek M. Williams, Cuyahoga Falls, OH (US); Matthew Calhoun, Stow, OH (US); George J. Picha, Breksville, OH (US)

(73) Assignee: APPLIED MEDICAL TECHNOLOGY, INC., Brecksville, OH (US)

( * ) Notice: Subject to any disclaimer, the term of this patent is extended or adjusted under 35 U.S.C. 154(b) by 883 days.

(21) Appl. No.: 14/554,860

(22) Filed: Nov. 26, 2014

(65) Prior Publication Data
US 2015/0157828 A1    Jun. 11, 2015

Related U.S. Application Data

(60) Provisional application No. 61/914,034, filed on Dec. 10, 2013.

(51) Int. Cl.
*A61M 16/04* (2006.01)

(52) U.S. Cl.
CPC .... *A61M 16/0488* (2013.01); *A61M 16/0497* (2013.01); *A61M 2207/00* (2013.01); *A61M 2209/088* (2013.01); *A61M 2210/0618* (2013.01)

(58) Field of Classification Search
CPC ...... A61M 16/0666; A61M 2210/0618; A61M 16/0488; A61M 25/02; A61M 16/0497; A61M 2209/088; A61M 2207/00
See application file for complete search history.

(56) References Cited

U.S. PATENT DOCUMENTS

| | | |
|---|---|---|
| 3,420,237 A | 1/1969 | Fortay |
| 4,114,626 A | 9/1978 | Beran |
| 4,282,871 A | 8/1981 | Chodorow et al. |
| 4,318,404 A | 3/1982 | Cunningham |
| 4,778,448 A | 10/1988 | Meer |
| 4,790,809 A | 12/1988 | Kuntz |
| 4,823,789 A | 4/1989 | Beisang, III |
| 5,021,043 A | 6/1991 | Becker et al. |

(Continued)

OTHER PUBLICATIONS

International Search Report for Corresponding Application No. PCT/US2014/067663; dated Mar. 31, 2015.

*Primary Examiner* — Bhisma Mehta
*Assistant Examiner* — Hamza A Darb
(74) *Attorney, Agent, or Firm* — Pearne & Gordon, LLP (57) ABSTRACT

A bridle catheter for installation into the nasal cavity of a patient comprises a tubular portion, a tape portion having a flattened geometry, and a transition zone located where the tubular portion meets the tape portion. A magnet is operatively attached in an open end of the tubular portion and secured therein so as to inhibit movement. A non-elastic member is integral with at least the tape portion and extends at least partially along a length thereof. In one example, the non-elastic member extends along substantially all of the tubular portion and tape portion. In another example, the non-elastic member comprises at least one of a ribbon or at least one fiber. A bridle catheter system is also provided that further comprises a stylet and a probe with a second magnet. A method of making the bridle catheter is further provided.

20 Claims, 5 Drawing Sheets

(56) References Cited

U.S. PATENT DOCUMENTS

| | | |
|---|---|---|
| 5,097,827 A | 3/1992 | Izumi |
| 5,105,807 A | 4/1992 | Kahn et al. |
| 5,117,818 A | 6/1992 | Palfy |
| 5,185,005 A | 2/1993 | Ballantyne |
| 5,492,538 A | 2/1996 | Johlin, Jr. |
| 5,549,866 A * | 8/1996 | Grifols Lucas ..... B29C 67/0014 |
| | | 264/320 |
| 5,700,252 A | 12/1997 | Klingenstein |
| 5,735,272 A | 4/1998 | Dillon et al. |
| 5,782,828 A * | 7/1998 | Chen ................. A61B 18/1206 |
| | | 604/95.01 |
| 5,851,185 A | 12/1998 | Berns |
| 6,248,092 B1 | 6/2001 | Miraki et al. |
| 6,355,050 B1 | 3/2002 | Andreas et al. |
| 6,464,668 B1 | 10/2002 | Pace |
| 6,478,026 B1 | 11/2002 | Wood |
| 6,631,715 B2 * | 10/2003 | Kirn .................. A61M 16/0488 |
| | | 128/200.24 |
| 6,837,237 B2 | 1/2005 | Kirn |
| 7,534,228 B2 * | 5/2009 | Williams .............. A61M 25/02 |
| | | 128/200.24 |
| 8,709,018 B2 | 4/2014 | Williams et al. |
| 2002/0088905 A1 | 7/2002 | Hansen |
| 2002/0156430 A1 * | 10/2002 | Haarala ............. A61M 25/0075 |
| | | 604/247 |
| 2003/0004493 A1 * | 1/2003 | Casey ................. A61M 25/005 |
| | | 604/525 |
| 2004/0069309 A1 * | 4/2004 | Kirn .................. A61M 16/0488 |
| | | 128/207.18 |
| 2005/0236001 A1 | 10/2005 | Williams |
| 2014/0041666 A1 * | 2/2014 | Slaga ................ A61M 16/0683 |
| | | 128/207.18 |

\* cited by examiner

BRIDLE CATHETER

CROSS-REFERENCE TO RELATED APPLICATIONS

This application claims the benefit of U.S. Provisional Application No. 61/914,034, filed Dec. 10, 2013, the entire disclosure of which is hereby incorporated herein by reference.

FIELD OF THE INVENTION

The present application relates generally to a nasal tube retaining system, often referred to as a bridle catheter.

BACKGROUND OF THE INVENTION

In an effort to prevent premature pullouts, nasoenteric tubes are often fixed in place using a wide variety of bridling systems. Most of these systems are difficult to place in the patient, requiring great dexterity by the physician and present unusual discomfort for the patient.

Known bridle systems have already proven to be of great value for hospitals and typically lead to better patient outcomes. The quick and easy placement of the bridle in a patient, the lack of adhesive on the patient's face, and the "negative feedback" (aka: self-induced pain) associated with patient attempts to extubate themselves are the hallmarks of known bridle systems. Example conventional bridle systems are taught in U.S. Pat. Nos. 6,631,715 and 6,837,237 to Kirn. One example bridle system presently in use is taught by U.S. Pat. No. 7,534,228 to Williams, the disclosure of which is incorporated herein by reference in its entirety.

BRIEF SUMMARY OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect of the present invention, a bridle catheter comprises a flexible elongated member extending between a first end and a second end, and comprises a tubular portion associated with the first end and a tape portion associated with the second end. The tubular portion has a tubular geometry and the tape portion has a flattened geometry. The elongated member further comprises a transition zone located where the tubular portion meets the tape portion. A magnet is operatively attached in an open end of the tubular portion, and the magnet is inserted a distance into the open end of the tubular portion and secured therein so as to inhibit movement of the magnet relative to the open end of the tubular portion. A non-elastic member is integral with the elongated member and extends along at least part of a length thereof.

In accordance with another aspect of the present invention, a bridle catheter system is provided for installing a bridle catheter in the nasal cavity of a patient, comprising a flexible elongated bridle catheter comprising a tubular portion, a tape portion having a flattened geometry, and a transition zone located where the tubular portion meets the tape portion. The tubular portion, transition zone, and tape portion are unitary. A magnet is operatively attached in an open end of the tubular portion and secured therein so as to inhibit movement of the magnet relative to the open end of the tubular portion. A non-elastic member is embedded within at least the tape portion and extends at least partially along a length thereof. A stylet is positioned in an opening of the transition zone of the elongated bridle catheter. A probe has a second magnet installed in an end thereof that has a first polarity extending axially and outwardly from the probe that is opposite to a second polarity of the magnet extending axially and outwardly from the tubular portion, such that the two magnets readily attract each other when in close proximity. The bridle catheter is configured for insertion into a first nare of a patient and extends substantially behind a vomer bone of the patient, and the probe is configured for insertion into a second nare of the patient and extends substantially behind the vomer bone of the patient, such that the second magnet of the probe mates with the magnet of the bridle catheter in order to permit the bridle catheter to be pulled from the second nare of the patient by the probe.

In accordance with another aspect of the present invention, a method of making a bridle catheter is provided, comprising the step of providing a flexible tubing that has a non-elastic member embedded into a wall of the tubing, wherein the tubing has an original cross-sectional area. The method further comprises the step of heating and flattening a portion of the tubing such that the tubing defines a tubular portion at a first end and a flattened tape portion at a second end, with a transition zone between the tubular portion and tape portion. The tubular portion has a cross-sectional area substantially equal to the original cross-sectional area, and the tape portion has a reduced cross-sectional area less than the original cross-sectional area. The method further comprises the step of installing a magnet into an open end of the tubular portion. The method further comprises the step of forming an opening through the transition zone to permit entry of a stylet into a hollow interior of the tubular portion.

It is to be understood that both the foregoing general description and the following detailed description present example and explanatory embodiments of the invention, and are intended to provide an overview or framework for understanding the nature and character of the invention as it is claimed. The accompanying drawings are included to provide a further understanding of the invention and are incorporated into and constitute a part of this specification. The drawings illustrate various example embodiments of the invention, and together with the description, serve to explain the principles and operations of the invention.

BRIEF DESCRIPTION OF THE DRAWINGS

The foregoing and other aspects of the present invention will become apparent to those skilled in the art to which the present invention relates upon reading the following description with reference to the accompanying drawings, in which.

DESCRIPTION OF EXAMPLE EMBODIMENTS

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

The example described herein provides a retaining system that is inserted into the nasal cavity of a patient such that a loop is formed behind the vomer bone of a patient. The installation procedure shares similarities with U.S. Pat. No. 7,534,228 to Williams, the disclosure of which is incorporated herein by reference in its entirety. The retaining system remains in place behind the vomer bone and two ends of the loop extend from the nostrils, with one end extending from a first nostril and the other end extending from a second nostril. The ends may then be coupled together to form a loop and a variety of devices may be coupled to the loop and suspended from the loop, such as nasal tubes, endotracheal tubes, nasal trumpets and the like. The loop is made of a material that allows for prolonged use within a nasal cavity and is not easily removed from the nasal cavity unless removed by a professional. In particular, the loop is not easily torn and if a patient pulls on the loop, the patient feels pressure and possibly pain behind their vomer bone. This pain helps to deter removal of the loop from the patient's nasal cavity and, at the same time, helps to deter removal of the device that is suspended by the loop.

The loop is a flexible member that is inserted through a first nostril and retrieved through the other nostril. As such, the device has enough flexibility to bend behind the vomer bone so that it can be removed via the other nostril. In addition, the flexible member is generally non-elastic and does not stretch out over time. By contrast, an elastic or stretchy flexible member would permit a patient to potentially remove the device that is being held in place by the loop. The flexible member has an insertion end with a magnet positioned at its leading end and is retrieved from the first nostril via the second nostril with the use of a complementary magnet and a probe.

Once the flexible member is inserted into the first nostril such that it is positioned in the nasal cavity behind the vomer bone, a probe having a magnet for mating with the magnet of the flexible member is inserted into the second nostril until it reaches the rear of the nasal cavity behind the vomer bone. Due to the strong attraction between the two magnets, the magnets are attracted to one another when in close proximity such that they meet and attach to one another rather easily. Once the magnets are attached together, the probe can be removed from the second nostril to pull the flexible member and its magnet from the second nostril until a loop is formed that extends from the first nostril to the second nostril. The insertion portion, as will be explained below, may be removed from the nasal cavity such that only a flattened portion of the bridle remains. The ends of the bridle may then be clipped or tied together and may be coupled to a device, such as a nasal tube, ET tube, nasal trumpet, or the like.

As bridle systems have become more accepted in the marketplace, it is desired to be able to make the entire bridle system smaller so they can be used by smaller patients, for example. Many pediatric patients are fed solely with nasal-gastric (or nasal-jejunal) tubes and a smaller Bridle system would be more conducive to these patients. Other nasal tubes (such as oxygen cannulas, nasal trumpets, etc.) could benefit from a smaller Bridle system geared toward pediatric patients. The example bridle system may also be beneficial for endotracheal tube retainment, which may more easily incorporate a smaller bridle delivery system.

Bridles are often stated to be used "for the life of the nasal tube" or other device that they are coupled to. In order to meet the objective of making the bridle smaller and longer-lasting, the flexible catheter may be made smaller in diameter than existing bridles, the wall of the flexible catheter may be made very thin (e.g., thinner than existing bridles), and the bridle may remain extremely tear resistant. The material used in the system may be easily incorporated into the manufacturing assembly process, and the material used in the system is biocompatible and biologically inert—up to, at least, 30 days in the body exposed to mucosal membranes.

Due to the tighter bends in the nasopharynx of a child or other relatively small patient, both the flexible member (also referred to as a catheter) and the tape-like material should be extremely flexible and able to have tight radii of curvature. Oftentimes, when materials are flexible, they also have the characteristic of being elastic. The tape material used in the example system should be flexible, yet non-elastic in order to be an effective nasal tube anchoring system. Due to the tighter nasal passages in smaller patients, both the flexible catheter and the tape material should be slick and lubricious. If these materials cannot slide easily through the nasal passages, the magnets of the probe and flexible member may disconnect during placement; thus preventing the delivery of the bridle system. Therefore, the example bridle may easily incorporate hydrophilic coatings (or something equivalent in order to make the bridle slide more easily) into the material(s) used to create the flexible catheter and the tape. This would also facilitate the use of the example bridle for patients with a deviated septum, which already exhibit a restriction within the nasal passages.

The nasal tubes used in pediatric patients are very small (i.e., example medical sizes 5 French and 6 French). It is difficult to use a standard bridle clip on these tubes because bridle clips rely on friction to serve their purpose of anchoring. Small tubes have less surface area for friction, and bridle clips have the possibility of slightly pinching the tube and reducing flow through the nasal tube.

Since the tubing may be formed of a meltable material, such as a soft thermoplastic like polyurethane, the device that is created may allow the end user (or the manufacturer) to heat and melt the bridle to a thermoplastic nasal tube or other device that is being retained in the vicinity of the nose. A melting tool could be used to melt the bridle catheter to a nasal tube or another device to thereby permanently couple the bridle catheter thereto. In this manner, the tape can be heat sealed to a tube or other device such that presently known clips are no longer used. This would allow the end user to quickly bond the material to the nasal tube or another device using a custom heat-sealing bridle device (provided the nasal tube is made of polyurethane or a similar material that can melt and bond to the tape material of the bridle system). Use of a polymeric material instead of the use of umbilical tape in known devices may allow for the possibility of attaching or pre-attaching to the bridle tape portion. For example, nasal tubes that have the tape pre-attached, pre-sealed, and pre-melted, could be utilized. Alternatively, a clip could be molded into the nasal tube or the bridle such that is it no longer necessary to fumble for a clip and risk dropping it during installation. This heat-sealing system, unlike the current clip system, would not be affected by mucus, humidity, lubricants, nasal tube surfaces, or similar factors.

By incorporating some or all of these features into the example bridle system, a pediatric version of the device can be developed. In addition, these features can also be incorporated into adult versions of the bridle system to improve the overall performance of the bridle system.

The example bridle system may also incorporate a new material that is based upon a low-durometer polyurethane tubing that is coextruded with relatively small non-elastic fibers or ribbon. Low-durometer polyurethane, by nature, is soft, flexible, biocompatible, biologically inert and tear resistant. One type of polyurethane that is currently being used is qualified as a USP Class VI material. In addition, the chosen nylon fibers and colorants may also qualify as biocompatible materials. If desired, the polyurethane resin used to create the extruded tubing can have hydrophilic additives added to it before the extrusion process, or they can be applied using a dip-coating process afterward. This allows the flexible member to navigate tight nasal passages and septums that are deviated since the additives would render the tubing more slippery. In addition, if desired, the polyurethane used in the extrusion can be compounded with a variety of different colorants, hydrophilic coatings, and/or anti-microbial additives.

However, polyurethane is also relatively elastic. The small fibers or ribbon embedded into the wall of the single-lumen polyurethane tubing will allow the tubing to maintain its softness and flexibility, but virtually eliminate the inherent elastic characteristic of the polyurethane material. A polyurethane resin is used to create the extruded tubing. This resin can have anti-microbial additives added to it before the extrusion process. Alternatively, anti-microbial additives can be applied using a dip-coating process afterward.

The use of a low-durometer polyurethane tubing allows the bridle to be very tear resistant. As such the bridle system can be made even smaller in diameter because the wall thickness can be reduced. Even with reduced wall thickness, polyurethane can prevent tearing and stylet poke-throughs. Using a modified laminating machine, polyurethane tubing can be easily processed into a bridle component. The polyurethane section is flattened to provide a replacement for the umbilical tape of the existing bridle systems. The flattened polyurethane section is a thermoplastic material having a monofilament running along its length in order to deter stretching, which assists in reducing the attachment sites for infection-causing microorganisms. A conventional magnet stuffing fixture can quickly insert magnets. Thus, bridles may be produced at a much faster rate than current manufacturing methods allow. Other materials may alternatively be utilized for the tubing, including, but not limited to, thermoplastic elastomers (TPEs), such as polyurethane, styrenic block copolymers, including polystyrene butadiene styrene, and Styrene-butadiene-styrene block copolymer (SBSs) and Styrene Ethylbutylene Styrene (SEBs), such as thermoplastic copolymers, thermoplastic polyamides, Pebax, and the like.

Figure 1:
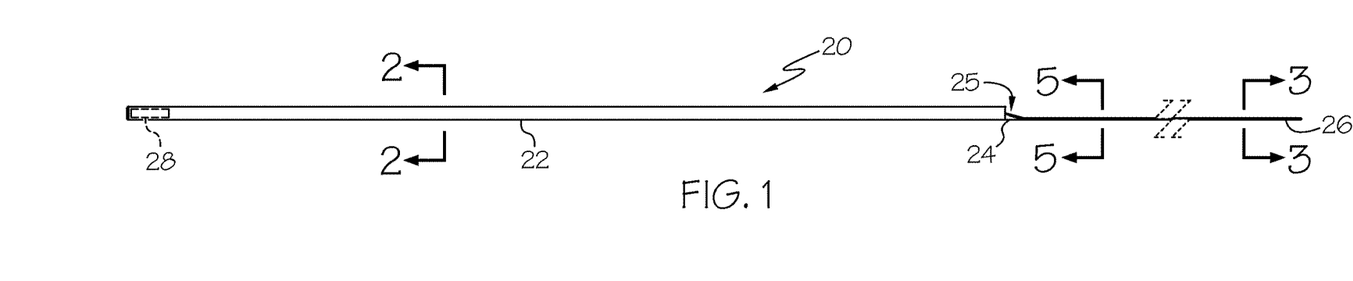
FIG. 1 is a side view of an example bridle catheter of the instant application.

Turning to FIG. 1, one example bridle catheter 20 for use with a nasal tube retaining system is shown. The example bridle catheter 20 has a tubular portion 22, a transition zone 24, and a tape portion 26. One example bridle may have an overall length of about 30 inches, with the tubular portion being about 5 inches, although it is contemplated that other dimensions may alternatively be used. The transition zone 24 is provided between the open tubular portion 22 and the flattened tape portion 26. In one example, the tape portion 26 shown was previously a tubular portion that has been flattened using heat, or other techniques for obtaining a tape portion 26. The tubular portion 22 remains tubular at an open end for insertion of a magnet 28 therein. Further, an opening 25 is installed in the transition zone 24 in order to permit the entry of a tool, such as a stylet, into the interior of the tubular portion 22. As will be described in greater detail herein, a non-elastic member, such as a fiber or ribbon, runs at least partially along the length of the bridle catheter, and may even run completely along the length of the bridle catheter. For example, the polyurethane tube can be co-extruded with fibers, such as nylon fibers, or a ribbon that is used to deter the bridle from stretching. More than one fiber or ribbon may be used, if desired. In one example, the fiber or ribbon can be centered within the flattened portion in order to deter twisting of the flattened portion.

Figure 15:
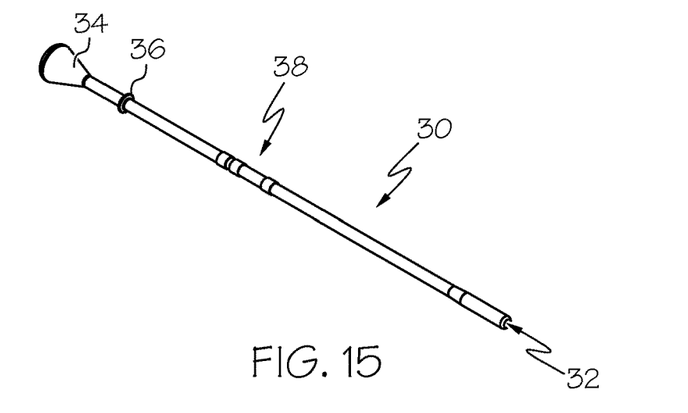
FIG. 15 is a perspective view of an example probe.
Figure 16:
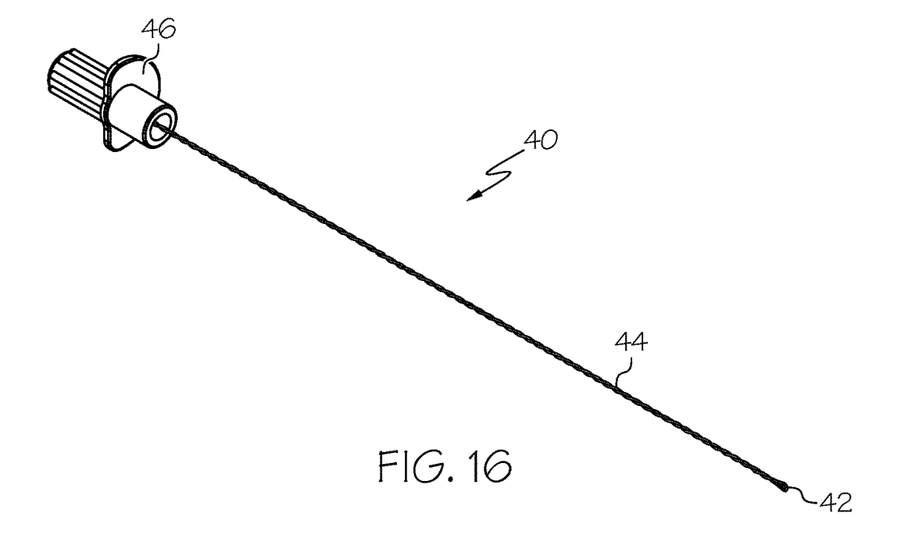
FIG. 16 is a perspective view of an example stylus.
Figure 17:
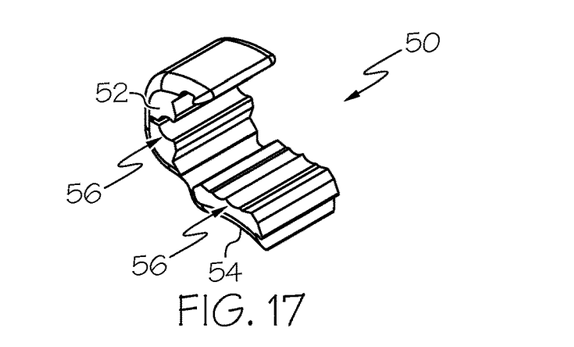
FIG. 17 is a perspective view of an example retention clip.

Additional elements of the nasal tube retaining system are shown in FIGS. 15-17. Typically, the system also includes a substantially rigid probe 30 with a magnet 32 at one end, and a stylet 40. A hole is formed in the transition zone 24 for permitting the insertion of an end 42 of the stylet 40 into a hollow interior of the tubular portion 22 of the bridle catheter 20. The transition zone 24 is generally smooth and permits easy entry of the end 42 of the stylet 40 into the tubular portion 22 to reduce interference that could otherwise deter the entry into or removal from the tubular portion 22 by the stylet 40.

The stylet 40 may include a wire 44 coated with PTFE or the similar material, and further includes a handle portion 46 that is of greater diameter than the wire 44 in order to provide a way to grip the stylet 40. Alternatively, the stylet 40 may also have a metal tip. In use, the stylet 40 is received into the opening 25 of the transition zone 24 and extends within the interior of the tubular portion 22 up to where the magnet 28 is positioned. In this manner, the stylet 40 provides a temporarily rigidity for maneuvering the otherwise flexible tubular portion 22 during insertion into a patient's nostril.

The probe 30, as shown in FIG. 15, includes the magnet 32 installed in a tubular opening at one end thereof. The magnet may be positioned in the end of the probe 30 using conventional magnet installation equipment. The probe 30 can have various geometries, and in one example has a frustoconical shape (e.g., trumpet-shaped) such that an enlarged portion 34 is positioned at the end of the probe 30 opposite the other end that includes the magnet 32. The enlarged portion 34 is utilized to prevent the probe 30 from being inserted too deeply into the nasal cavity of the patient. One or more grooves 36 may be provided on an outer surface of the probe to assist in gripping the probe. Similarly, indicating marks 38 may be provided on the outer surface to measure the depth the probe as it is inserted into the patient's nostril.

Briefly, a procedure for retrieving the bridle catheter 20 with the probe 30 and therefore placing the bridle catheter in the patient will be described in more detail below. In inserting the bridle catheter, the probe 30 is inserted into one nare, while the tubular portion 22 of the bridle catheter 20 is inserted into the other nare, using the stylet 40. The probe 30 and tubular portion 22 are maneuvered relative to each other until the magnet 28 of the bridle catheter 20 attaches to the magnet 32 of the probe 30 in the rear of the nasal cavity behind the vomer bone (e.g., about the posterior nasopharynx). The magnets 28, 32 preferably have reverse polarity to one another so that they readily attract to one another and attach together. The magnets 28, 32 may be rare earth magnets that are gold plated. While a pair of magnets is typically utilized for both the probe and the tubular portion of the catheter, it is contemplated that a metallic member could be utilized instead of a magnet, if desired, as long as the other portion of the insertion system utilizes a magnet that is attracted to the metallic member. Once the magnets 28, 32 attach, the stylet 40 is removed from the tubular portion 22, and then the probe 30 is pulled from the nare until both magnets are pulled from the nasal cavity, via a single nare, and the tape portion 26 remains positioned or looped behind the vomer bone and extends from each nare of the patient. The tubular portion 22 and/or transition zone 24 may optionally be cut away and discarded such that only the tape portion 26 remains in the nasal cavity and nostrils.

Finally, a bridle retention clip 50 (one example shown in FIG. 17) can be used to attach the exposed ends of the bridle catheter 20 to a nasal tube or other device, such as an endotracheal tube, oxygen cannula, or a nasal trumpet. The retention clip 50 can be any type of fastener, such as a clip, clasp, clamp, buckle, or the like. The shown retention clip 50 includes an openable member with two sides 52, 54 that are closable together via a hinge or the like to retain the bridle catheter 20. One or more channels 56 extend into either or both of the two sides to receive the exposed ends of the bridle catheter 20. Additional steps of the installation procedure, applicable for use with the instant bridle catheter, are described in U.S. Pat. No. 7,534,228 to Williams, the disclosure of which is incorporated herein by reference in its entirety.

Figure 2:
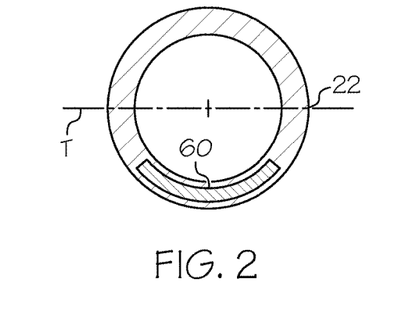
FIG. 2 is a sectional view of the tubular portion taken along line 2-2 of FIG. 1.
Figure 3:
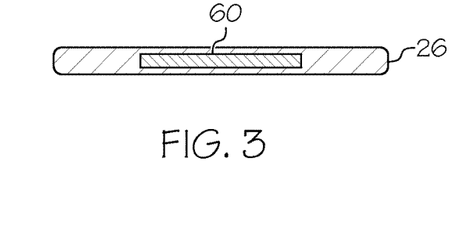
FIG. 3 is a sectional view of the tape portion taken along line 3-3 of FIG. 1.
Figure 4:
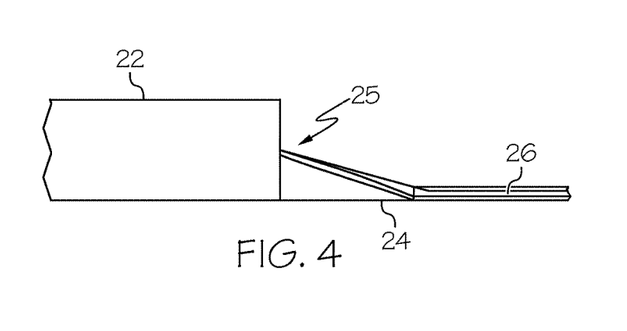
FIG. 4 is a side detail view of the transition zone of FIG. 1.
Figure 5:
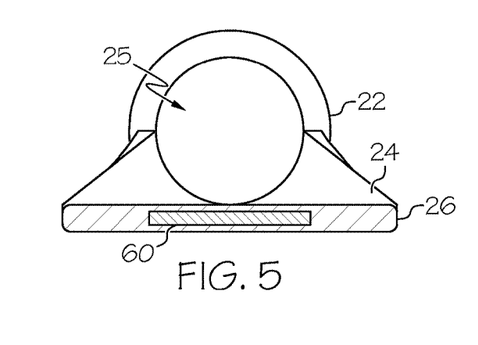
FIG. 5 is a sectional view taken along line 5-5 of FIG. 1 illustrating a front view of the transition zone.

Turning back to FIGS. 1-5, the bridle catheter 20 will now be described in greater detail. FIGS. 2, 3 and 5 depict an example where the bridle tubing includes a co-extruded ribbon that extends along the length of the tubular portion 22, transition zone 24, and tape portion 26. FIG. 4 also more readily shows a detail view of the transition zone 24 between the tubular portion 22 and the tape portion 26. As discussed above, the bridle catheter 20 starts as the tubular portion 22, and then during manufacturing a section of the tubular portion is flattened by heating or other process in order to form the transition zone 24 and tape portion 26. The tape portion 26 of the tube may be heat sealed such that it does not have an opening. The bridle catheter 20 forms a continuous structure from the tubular portion 22 through the tape portion 26. In an alternative embodiment, the tubular portion 22 and the tape portion 26 may be formed separately and secured together, such as by a butt-welding operation, adhesives, etc. In such an alternative example, ribbon or fiber reinforcement may be avoided in the tubular portion 22 since the tubular portion 22 will not remain in the nasal cavity after installation. Thus, a tubular portion 22 that does not have ribbon or fiber reinforcement may be butt-welded or otherwise secured to the tape portion 26 at the transition zone 24. The tape portion 26 may be separately formed as a coextruded tape portion that surrounds fibers or a ribbon within a polyurethane material in order to deter stretching of the tape portion 26, as described herein. As a result, the bridle catheter 20 is a unitary structure that is a monolithic structure or that includes multiple elements secured together.

Typically, the tape portion 26 is relatively longer than the tubular portion 22, especially since the tape portion 26 becomes the operative portion of the bridle once installed within the nostrils of a patient. The tape portion 26 extends from the transition zone 24 and is long enough to permit the tape portion 26 to extend from a patient's first nostril, behind the vomer bone of the patient, and out the patient's second nostril, with sufficient room leftover for attaching to the retention clip 50 or nasal tube. In one example, the tape portion 26 may be around 30 inches long and the tubular portion 22 may be around 5 inches long, although other lengths may alternatively be used. Alternatively, it is contemplated that a heat-sealing system may be used that would allow the end user (or manufacturer) to melt the tape portion 26 to any nasal tube. This would eliminate the need for a retention clip 50, and make the completed nasal retaining system as low profile as possible.

In the example shown in FIGS. 2, 3 and 5, a non-elastic member, such as an umbilical ribbon 60, is integral with the tubing that will eventually form the tubular portion 22 and tape portion 26. The ribbon 60 can be embedded and/or encapsulated in the material of the tubing. In one example, the non-elastic member can be co-extruded with the tubing. The ribbon 60 is non-elastic, at least along its longitudinal axis, so as to provide strength to the bridle catheter 20 along its length. In this manner, the tape portion 26 can be more easily manipulated through the patient's nostrils and can be properly secured afterwards. Additionally, the ribbon 60 is preferably highly flexible and able to have tight radii of curvature. Moreover, as shown in the contrasting sections of FIGS. 2-3, the ribbon 60 should be flexible along its transverse axis so as to correspond to the differing shapes of the tubular portion 22 (i.e., where the ribbon 60 takes on a "U"-shaped geometry) and the tape portion 26 (i.e., where the ribbon 60 takes on a generally flattened geometry). The non-elastic member extends along at least part of the length of the tubing, and may run completely along the length of the tubing. The non-elastic member may be continuous or discontinuous.

Flattening of the tube can be provided by a heating device, such as a laminating machine or similar device that combines a heating element with rollers. One example device that may be a laminator provided by the company Fellowes. Although described as a laminating machine, it is understood that no other elements are being laminated together in the conventional sense, or otherwise secured to the bridle; instead, the laminating machine or the like is used because it applies heat to items passing therethrough while simultaneously applying a compressive force as the item passes between two or more rotating rollers. Alternatively, a heated press having a flattening device could also be used.

Upon proceeding through the laminating machine, the tube is flattened, compressed and/or melted after the transition zone 24 to thereby create a distinct tubular portion 22 and tape portion 26. The tubular portion 22 has a cross-sectional area substantially equal to the original cross-sectional area of the tubing, and the flattened tape portion 26 has a reduced cross-sectional area less than the original cross-sectional area. During heating, the flattened tube may bend, twist or form waves due to different properties between the fibers and the tubular member material. In order to deter excessive bending, twisting, and/or waves, the non-elastic member or may be oriented about the middle of the flattened tubing, although this is not absolutely required. The non-elastic member could be positioned elsewhere in the cross-section. Indeed, if a particular bending, twisting, and/or waves occurs, the non-elastic member could be strategically placed within the flattened tubing so as to counteract such non-desired properties. Once a desired length of the tubing portion 26 is formed, the bridle catheter 20 can be removed from the manufacturing machine in the reverse direction so that part of the tubing remains as the tubular portion 22. It should also be appreciated that in the alternative, the tape portion 26 of the tube is not flattened but retains a tubular geometry. This tubular geometry may be similar to that of the tubular portion 22.

Turning now to FIGS. 6-10, another example bridle is shown in which the previously-described ribbon 60 is replaced by at least one fiber 62. It is otherwise understood that the remainder of the bridle is similar to that previously described. As used herein, it is contemplated that a fiber is a relatively fine, threadlike structure or slender filament, while a ribbon is a long, narrow strip. The fiber can be a monofilament, or a multi-filament structure. The use of a monofilament material, as opposed to a ribbon, can reduce the surface area of the bridle attachment system to thereby reduce the possibility of infection from microorganisms. As shown, the non-elastic member can comprise two nylon fibers 62 that are co-extruded with the tubing, and may be relatively small in diameter. The two nylon fibers 62 are shown being positioned relatively next to each another so that they are positioned only on one half or one side of the circumference of the tube (i.e., arranged at one side of the transverse axis or centerline T, see FIG. 7). As a result, when the tape portion 26 is formed by flattening, compressing, and melting a part of the tube, the two nylon fibers 62 remain relatively centered within the resulting tape portion 26. However, it is understood that the fibers 62 can be positioned variously about the flattened portion 26. It is further contemplated that the fibers could be made from other materials, such as Kevlar, polycarbonate, polyethylene, polypropylene, polyester, combinations thereof, or the like.

When heating, compressing, and melting the tube, the nylon fibers 62 (or ribbon 60) do not breech the surface of the polyurethane tubing at any point along the length of the tubular portion 22, transition zone 24, or tape portion 26. In addition, the fibers 62 may bond with the material of the tubing during heating to further strengthen the bond between the tubing and the nylon fibers. The tubing may be opaque, or could be transparent, if desired. The nylon fibers and/or ribbon coextruded with the tape help to deter longitudinal stretching and are preferably continuous along the length of the tape/tubing.

Figure 11A:
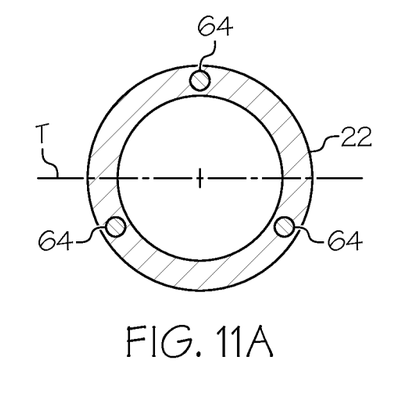
FIGS. 11A-11B are similar to FIG. 7, but show alternative example fiber arrangements.
Figure 11B:
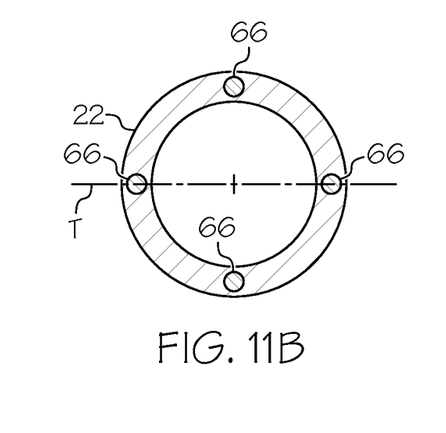

While two fibers 62 are shown, a single fiber could be utilized, or even more than two fibers could be used. Turning to FIGS. 11A-11B, other example fiber arrangements are shown. In FIG. 11A, three total fibers 64 are shown to be embedded within the tubular portion 22. Similarly, in FIG. 11B, four total fibers 66 are shown to be embedded within the tubular portion 22. When flattened or compressed to create the tape portion 26, the three or four fibers 64, 66 would be arranged generally along a transverse line within the tape portion 26. The fibers 64, 66 are preferably arranged symmetrically about the tubular portion 22, such as symmetrically about a central axis of the tube, as shown, although it is understood that the fibers could be arranged variously as desired, and may alternatively be positioned at other positions around the circumference.

Turning back to FIGS. 4 and 9, the transition zone 24 is formed between the tubular portion 22 and the tape portion 26 of the bridle catheter. The transition zone 24 is naturally created at the point where heating/flattening of the tube stops. In some cases, it may be desirable to pinch or otherwise greatly compress the tube at the desired location of the transition zone 24 in order to provide a more definite transition area. The pinching may be performed while the tubing is still hot from the laminator, and may be performed by a tool, or even by a user's fingers. Pinching is optional, but may in some instances create a cleaner, more defined transition between the tubular portion 22 and the tape portion 26.

Figure 9:
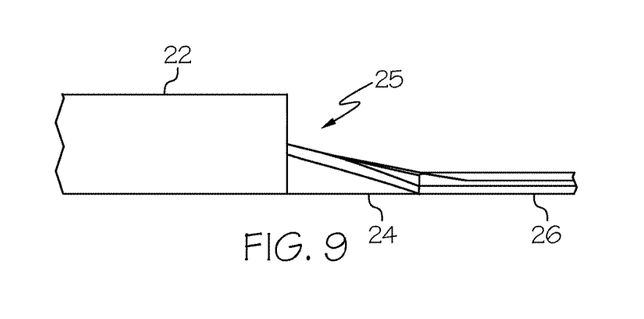
FIG. 9 is a side detail view of the transition zone of FIG. 6.
Figure 12:
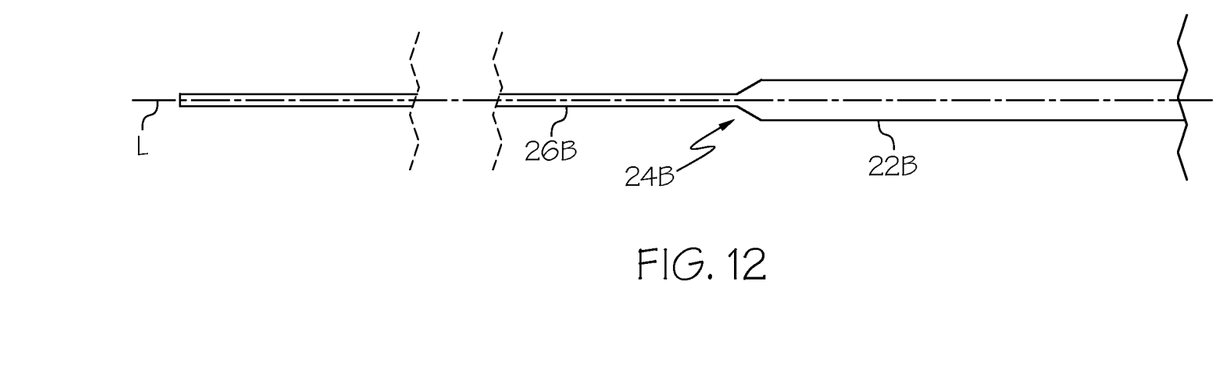
FIG. 12 is similar to FIGS. 4 and 9, but shows an alternative transition zone geometry.

Other transition zone 24 geometry can also be formed using other techniques. In FIGS. 4 and 9, the transition zone 24 is formed by compression applied from a single side (e.g., the top side in the shown example). Thus, the transition zone 24 has a ramped geometry that extends between the flattened, reduced-thickness tape portion 26 and the original-sized tubular portion 22. However, as shown in FIG. 12, the transition zone 24B can be vertically centered along the central longitudinal axis L of the tube. For example, the transition zone 24B can be created by a pinching or compression applied from both of the top and bottom directions (and/or even one or more lateral directions). This can provide various benefits, such as a more even heating and compression of the tubular portion 22B and resulting formation of the tape portion 26B. A centered tape portion 26B may also be useful when multiple ribbon 60 or fibers 64, 66 are used about the circumference of the tube (e.g., see FIGS. 11A-11B).

Figure 10:
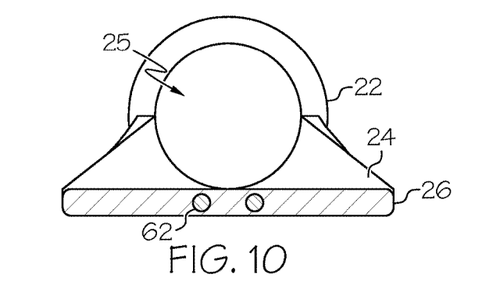
FIG. 10 is a sectional view taken along line 10-10 of FIG. 6 illustrating a front view of the transition zone.
Figure 13:
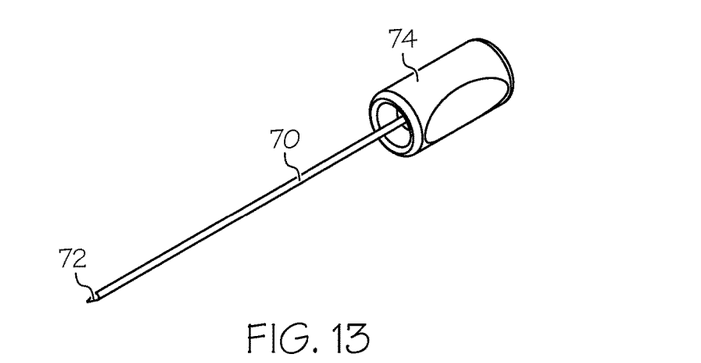
FIG. 13 is a perspective view of an example lumen poke through tool.

As discussed above, an opening 25 or hole is formed in the tubing at the transition zone 24 in order to permit the entry of a stiffened stylet 40 into the tubular portion 22. This stylet 40 is inserted during insertion of the tubular portion 22 into the first nostril, and temporarily increases the stiffness of the tubular portion 22 so that it can be more easily manipulated to reach the rear of the nasal cavity. Once the magnets 28, 32 of the tubular portion 22 and probe 30 connect together, the stylet 40 is removed and the tubular portion 22 again portion becomes flexible. In order to create the opening 25 for the entry of the stylet 40 in the transition zone 24, a hole is created using a lumen poke through tool 70, as shown in FIG. 13. The lumen poke through tool 70 has a pointed tip 72, a shaft, and a handle 74. The pointed tip 72 is heated in order to permit the lumen tip to poke through the tubular portion 22 at the transition zone 24. The pointed tip 72 is inserted through the solid tubular portion 22 in the vicinity of the arrowhead of reference number 25 as shown in FIGS. 4 and 9. Since the pointed tip 72 of the lumen poke through tool 70 is heated, it permits for a relatively smooth, evenly shaped hole to be created in the transition zone 24 in order to permit easy entry of the stylet 40 into the tube. FIGS. 5 and 10 show example openings 25 created at the transition zone 24. Preferably, the pointed tip 72 and shaft are inserted into the tubular portion 22 generally parallel with, or at a relatively small angle to, the longitudinal axis of the tubular portion 22. The shaft and pointed tip 72 are preferably made of a material that may be heated and retain heat for enough time in order to permit the opening of a hole in the tubular portion 22. The shaft and pointed tip 72 may be made of a metal material, for example. Preferably, the handle 74 is made of a different material that resists heat conduction to protect a user's hand. The handle 74 of the lumen poke through tool 70 may include a surface treatment, such as recesses, that permit for easy handling by a user. It is further contemplated that the lumen poke through tool 70 may also be suitably modified for use in an automated manufacturing operation.

Figure 14A:
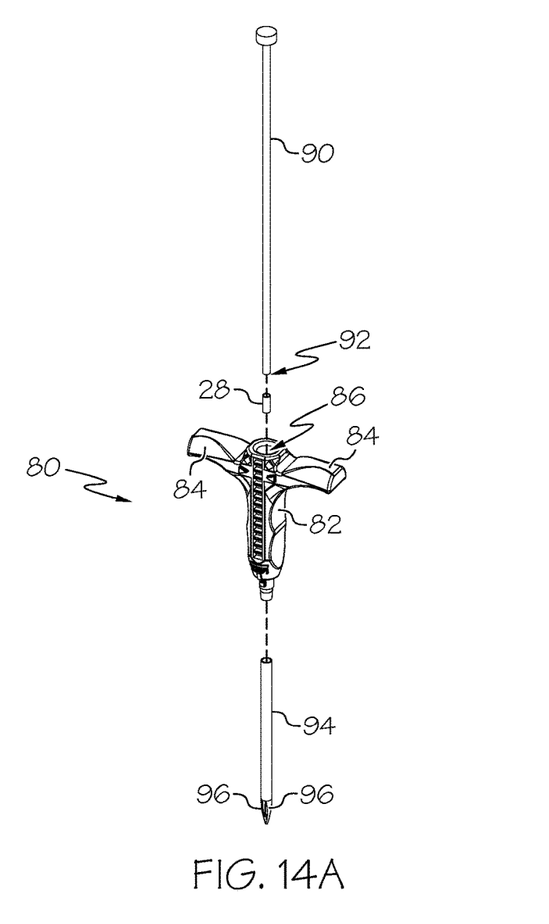
FIGS. 14A-14B are perspective views of an example magnet insertion tool.
Figure 14B:
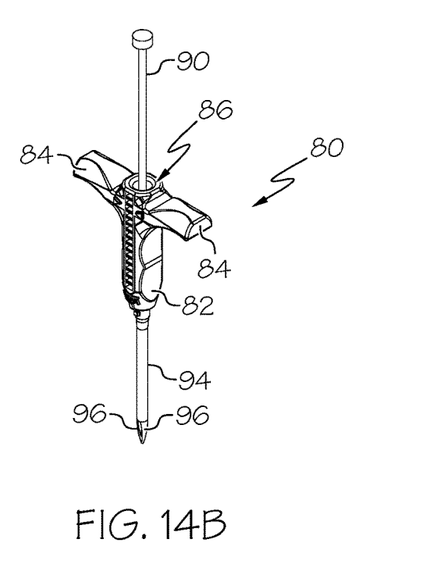

Assembly of the magnet 28 into an end of the tubular portion 22 (e.g., see FIGS. 1 and 6) will now be discussed with reference to FIGS. 14A-14B. Generally, the end of the tubular portion 22 is pliable and flexible, which permits the end to be temporarily expanded by an external force to provide an enlarged opening to receive the magnet 28. The magnet 28 is cylindrical and may be inserted by using a magnet insertion tool 80. The magnet insertion tool 80 includes a main body 82 with a handle portion 84 to facilitate manipulation of the magnet insertion tool 80 by a user. As shown, the body 82 can include a pair of handle portions 84, each being configured to receive one of a pair of adjacent fingers of a user's hand while a central portion of the body 82 is retained between the adjacent fingers. In addition or alternatively, the central portion can further include one or more contoured finger grips configured to help retain the user's fingers securely on the handles 84. A central aperture 86 extends completely through the body 82 from one end to the other, and can include various cross-sectional geometries, such as a circular cross-section, through other geometries can also be used (e.g., triangular, square, polygonal, etc.). Additionally, the cross-sectional geometry can vary. For example, as shown in FIG. 14A, an upper portion of the cross-sectional geometry of the aperture 86 can taper from a relatively larger diameter to a relatively smaller diameter at a lower portion thereof. Thus, the relatively larger diameter of the tapered portion can facilitate insertion of a push rod 90 within the body 82, while the relatively smaller diameter can facilitate alignment and stabilization of the push rod 90 as it extends through and out of the aperture 86.

The magnet 28 is coupled to the end 92 of the push rod 90, such as by a magnetic connection, adhesive connection, or other temporary coupling. Once the magnet 28 is axially aligned with the push rod 90, the magnet 28 and push rod 90 are inserted together into the upper open end of the magnet insertion tool 80. The push rod 90 is then passed through the aperture 86 of the insertion tool 80, as shown in FIG. 14B. The insertion tool 80 further comprises a lower tubular portion 94 with at least two flexible prongs 96 or arms positioned at the lower end thereof. The lower tubular portion 94 is coupled to the body 82 of the insertion tool 80 and is in communication with the aperture 86, preferably in a co-axial arrangement. The two prongs 96 are resiliently biased towards each other in a closed position that is configured to resist inadvertent removal of the magnet 28 from the lower tubular portion 94. For example, the two prongs 96 taper towards a cross-sectional area less than that of the magnet 28 to thereby retain the magnet 28 within the lower tubular portion 94. The two prongs 96 further have a tapered geometry that provides a pointed tip to assist with insertion into the tubular portion 22 of the bridle catheter 20.

During assembly, the two prongs 96 are inserted into the end of the tubular portion 22 of the bridle catheter 20. Since the prongs 96 have a diameter greater than that of the tubular portion 22, the pointed tip is inserted into the end of the tubular portion 22 until the prongs 96 elastically spread or stretch the end of the tubing open. Next, the push rod 90 and magnet 28 are inserted through the interior aperture 86 of the body 82 of the insertion tool 80 until the magnet 28 is present in the opening between the prongs 96. Once the magnet 28 is present between the opening of the prongs 96 and the tubing end is spread open by the prongs 96, the push rod 90 is further pressed upon to push the magnet 28 into the opening created in the end tubing between the prongs 96. A stop 91 can be provided at an upper end of the push rod 90 to limit an insertion distance into the aperture 86 of the body 82. Passage of the magnet 28 through the prongs 96 causes the prongs 96 to temporarily separate apart to permit passage of the magnet 28 therebetween. Once the magnet 28 is in place in the tubing, the prongs 96 are removed from the tubing while the magnet 28 remains in the end of the tubular portion 22 due to friction and/or an interference fit, adhesives, fasteners, or even through a locking connection between the exterior of the magnet 28 and the interior of the tubing. After insertion, the magnet 28 may be fully installed into the tubular portion 22, or part of the magnet may protrude from the end of the tubing. It is further contemplated that a similar assembly operation may be used to insert the magnet 32 into an end of the probe 30, or alternatively the magnet 32 can assembled using adhesives, molding, etc.

Figure 6:
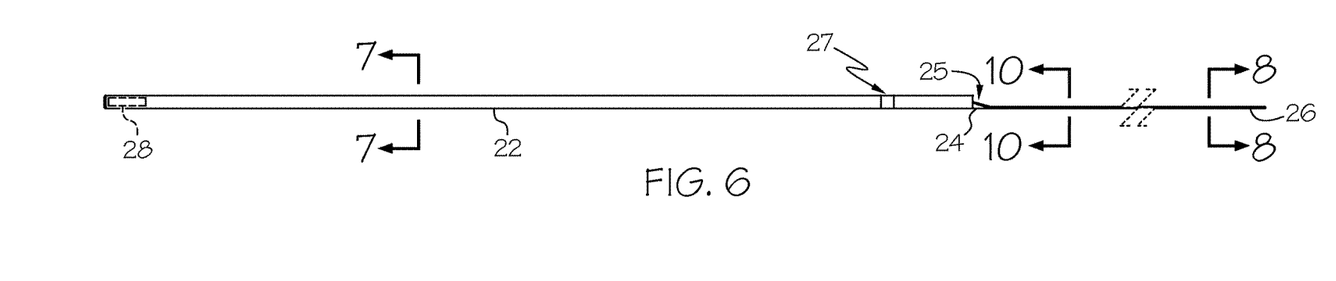
FIG. 6 is a side view of another example bridle catheter of the instant application.
Figure 7:
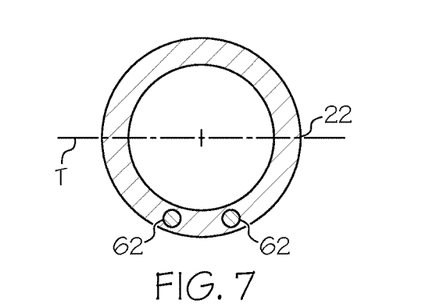
FIG. 7 is a sectional view of the tubular portion taken along line 7-7 of FIG. 6.
Figure 8:
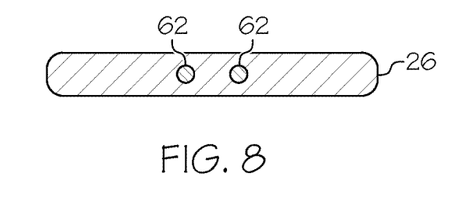
FIG. 8 is a sectional view of the tape portion taken along line 8-8 of FIG. 6.

As discussed above, the probe 30 can include marks 38 either printed on or molded directly in the probe on the outer surface to measure the depth the probe as it is inserted into the patient's nostril. Similarly, as shown in FIG. 6, the tubular portion 22 can include one or more markings 27 or rings, such as a blackened pad printed ring, that is coupled to the tubing in proximity to the transition zone 24. The marking 27 is used to align the distal tips of the probe and tube depth-wise during insertion into the nasal cavity. Since the end tips of the probe 30 and tubular portion 22 are hidden from view during placement in the patient's nostrils, the pad printed marking 27 or ring may be used to judge the depth from the exterior view of the caregiver. When both of the probe 30 and the tubular portion 22 have markings to indicate depth, the tip of the tube and the probe can be aligned at matching depths when the two similar marks 27, 38 are aligned. Thus, a plurality of corresponding markings 27, 38 can be provided, and may include corresponding indicia to enable a user to match them. A polyurethane-compatible pad print ink can be used to create the alignment mark(s) 27.

The polyurethane tubing for the improved example bridle is processed and assembled differently than previous versions of the prior art system. Examples of steps for assembling the improved bridle system can include, but are not limited to, the following. The polyurethane tubing is first coextruded with ribbon or small diameter fibers such that the ribbon or fibers are embedded into the tubing wall. In an example that was produced, two nylon fibers were coextruded with the tubing that was small in diameter. Once the polyurethane tube has been extruded and cured completely, the tube is heated and flattened to form the tape portion. One method for heating and flattening the tape portion of the bridle may be accomplished with a modified laminating machine, which allows for heating and flattening the tubing simultaneously. A lumen poke through tool is used to form an opening or hole through the transition zone to provide an opening for a stylet. A magnet insertion tool may be used to insert a rare earth magnet into the tubing end of the tubular portion. Adhesives may be avoided as the polyurethane is elastic enough to constrict around the outside diameter of the magnet. Alternatively, an adhesive may be used to assist in retaining the magnet.

The term "substantially," if used herein, is a term of estimation.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

What is claimed is:

1. A bridle catheter comprising:
a flexible elongated member extending between a first end and a second end, comprising a tubular portion associated with the first end and a tape portion associated with the second end, with the tubular portion having a tubular geometry and the tape portion having a flattened or tubular geometry sufficient for movement into and through a first nare to a second nare and then out from the second nare, and the elongated member further comprising a transition zone located where the tubular portion meets the tape portion;
a magnet operatively attached in an open end of the tubular portion, the magnet being inserted a distance into said open end of the tubular portion and secured therein so as to inhibit movement of the magnet relative to the open end of the tubular portion; and
a non-elastic member that is integral with the elongated member and extends along at least part of a length thereof.

2. The bridle catheter of claim 1, wherein the elongated member comprises a low-durometer polyurethane or a thermoplastic elastomer.

3. The bridle catheter of claim 2, wherein the elongated member is tear-resistant.

4. The bridle catheter of claim 1, wherein the non-elastic member is co-extruded with the elongated member and extends along substantially the entire length of the elongated member.

5. The bridle catheter of claim 1, wherein the non-elastic member comprises at least one ribbon or at least one fiber.

6. The bridle catheter of claim 5, wherein the non-elastic member comprises a plurality of separate fibers.

7. The bridle catheter of claim 6, wherein the tubular portion comprises a transverse axis, and all of the plurality of fibers are located at one side of the transverse axis.

8. The bridle catheter of claim 5, wherein the at least one ribbon is non-elastic along a longitudinal axis, and is flexible along a transverse axis.

9. The bridle catheter of claim 1, wherein the tubular portion, transition zone, and tape portion together comprise a monolithic structure.

10. The bridle catheter of claim 1, further comprising an opening extending through the transition zone that permits insertion of a stylus into a hollow interior of the tubular portion.

11. The bridle catheter of claim 1, wherein the magnet is retained within the end of the tubular portion by friction, by adhesive or by a combination thereof.

12. The bridle catheter of claim 1, wherein the elongated member is made of a biocompatible material that is coated or embedded with one or more of an anti-microbial compound, an anti-bacterial compound, and a hydrophilic compound.

13. The bridle catheter of claim 1, wherein the tape portion has the flattened geometry.

14. A bridle catheter system for installing a bridle catheter in the nasal cavity of a patient, comprising:
a flexible elongated bridle catheter comprising:
a tubular portion, a tape portion having a flattened or tubular geometry, and a transition zone located where the tubular portion meets the tape portion, the tubular portion, transition zone, and tape portion being unitary;
a magnet operatively attached in an open end of the tubular portion and secured therein so as to inhibit movement of the magnet relative to the open end of the tubular portion; and
a non-elastic member that is embedded within at least the tape portion and extends at least partially along a length thereof;
a stylet positioned in an opening of the transition zone of the elongated bridle catheter; and
a probe having a second magnet installed in an end thereof that has a first polarity extending axially and outwardly from the probe that is opposite to a second polarity of the magnet extending axially and outwardly from the tubular portion, such that the two magnets readily attract each other when in close proximity,
wherein the bridle catheter is configured for insertion into a first nare of a patient and extends substantially behind a vomer bone of the patient, and the probe is configured for insertion into a second nare of the patient and extends substantially behind the vomer bone of the patient such that the second magnet of the probe mates with the magnet of the bridle catheter in order to permit the bridle catheter to be pulled from the second nare of the patient by the probe.

15. The bridle catheter system of claim 14, further comprising a bridle retention clip to couple the bridle catheter to a nasal tube or another device.

16. The bridle catheter system of claim 14, wherein the bridle catheter is melted to a nasal tube or another device, thereby permanently coupling the bridle catheter to said nasal tube or another device.

17. The bridle catheter system of claim 14, further comprising a magnet insertion tool comprising a push rod and lower tubular portion with at least two prongs that are insertable into said open end of the tubular portion,
wherein the at least two prongs taper towards a cross-sectional area less than that of the magnet to thereby retain the magnet within the lower tubular portion, and
wherein the at least two prongs are insertable into said open end of the tubular portion and the push rod is configured to push said magnet past said at least two prongs and into said open end of the tubular portion.

18. The bridle catheter system of claim 14, wherein the flattened or tubular geometry of the tape portion is sufficient for movement through a first nare and then out from a second nare.

19. A bridle catheter comprising:
a flexible elongated member, comprising:
a first portion having a tubular geometry and a hollow interior;
a second portion having a tubular geometry; and
a transition zone located where the first portion meets the second portion, the transition zone having an opening that permits insertion of a stylet into the hollow interior of the first portion;
a magnet operatively attached in an open end of the first portion, said open end being at an end of the first portion opposite the transition zone, and the magnet being inserted a distance into said open end of the first portion and secured therein so as to inhibit movement of the magnet relative to the open end of the first portion; and a non-elastic member that is integral with the elongated member and that extends along at least part of a length thereof.

20. The bridle catheter of claim 19, wherein the tubular geometry of the second portion is sufficient for movement into a first nare through to a second nare and then out from the second nare.

* * * * *

UNITED STATES PATENT AND TRADEMARK OFFICE
CERTIFICATE OF CORRECTION

PATENT NO. : 10,314,994 B2  
APPLICATION NO. : 14/554860  
DATED : June 11, 2019  
INVENTOR(S) : Grant Wesley Phillips et al.

Page 1 of 1

It is certified that error appears in the above-identified patent and that said Letters Patent is hereby corrected as shown below:

On the Title Page

Item (72), Inventors, "Breksville, OH (US)" should read -- Brecksville, OH (US) --

Signed and Sealed this  
Seventeenth Day of September, 2019

Andrei Iancu  
*Director of the United States Patent and Trademark Office*